United States Patent [19]

Hagemann et al.

[11] Patent Number: 5,211,957
[45] Date of Patent: May 18, 1993

[54] SOLID RAPIDLY DISINTEGRATING DOSAGE FORM

[75] Inventors: Ruth Hagemann, Allschwil; Dagmar Wirth, Dottikon, both of Switzerland; Henri-Julien Bronner, Hésingue, France

[73] Assignee: Ciba-Geigy Corporation, Ardsley, N.Y.

[21] Appl. No.: 915,050

[22] Filed: Jul. 16, 1992

Related U.S. Application Data

[63] Continuation of Ser. No. 692,803, Apr. 24, 1991, abandoned, which is a continuation of Ser. No. 324,931, Mar. 19, 1989, abandoned.

[30] Foreign Application Priority Data

Mar. 25, 1988 [CH] Switzerland .................. 1138/88

[51] Int. Cl.$^5$ ............................................. A61L 9/46
[52] U.S. Cl. ................................. 424/466; 424/469; 424/470
[58] Field of Search ............... 424/466, 473, 494, 469, 424/470

[56] References Cited

U.S. PATENT DOCUMENTS

| | | | |
|---|---|---|---|
| 4,265,874 | 5/1981 | Bonsen et al. | 424/466 |
| 4,292,319 | 9/1981 | Tauber et al. | 514/220 |
| 4,847,093 | 7/1989 | Ayer et al. | 424/473 |
| 4,871,549 | 10/1989 | Ueda et al. | 424/494 |

FOREIGN PATENT DOCUMENTS

| | | |
|---|---|---|
| 255002 | 7/1986 | European Pat. Off. . |
| 203768 | 12/1986 | European Pat. Off. . |
| 2573310 | 3/1988 | European Pat. Off. . |
| 3607339 | 9/1987 | Fed. Rep. of Germany . |

OTHER PUBLICATIONS

Controlled Drug Delivery: Fundamentals and Applications 2nd ed. Dekker, New York, p. 140 (1987).
Specialized Drug Delivery Systems: Manufacturing and Production Technology Dekker, New York p. 333 (1990).
Martindale: The Extra Pharmacopoeia, The Pharmaceutical Press, London (1989).
Remington's Pharmaceutical Sciences, Mack Press New York (1985).
Derwent Abstract 87-307930/44 of EP 243,521 (1987).
Derwent Abstract 82-39785E/20 of EP 52076 (1982).
Derwent Abstract 86-341315/52 of EP 207,041 (1986).

*Primary Examiner*—Thurman K. Page
*Assistant Examiner*—Leon R. Horne
*Attorney, Agent, or Firm*—Irving M. Fishman; Karen G. Kaiser

[57] ABSTRACT

The invention relates to a solid, rapidly disintegrating dosage form in the form of effervescent tablets for producing an aqueous suspension of diclofenac for peroral administration. The dosage form contains diclofenac in micronised form provided with a permeable, swellable coating, together with pharmaceutical excipients.

4 Claims, No Drawings

SOLID RAPIDLY DISINTEGRATING DOSAGE FORM

This application is a continuation of application Ser. No. 692,803, filed Apr. 24, 1991, and now abandoned which is a continuation of 07/324/931 filed Mar. 17, 1989, now abandoned.

The present invention relates to effervescent tablets for producing an aqueous suspension of diclofenac, or a salt thereof, suitable for peroral administration, which tablets provide immediate or delayed release of the active drug. The invention further relates to the suspension obtainable from the disintegration of this dosage form in aqueous phase, to diclofenac, or a salt thereof, which is present in micronised form in the effervescent tablet and in the aqueous suspension obtainable therefrom and which is provided with a permeable, swellable coating, to a process for the preparation of said effervescent tablets and to the use thereof.

A variety of therapeutic agents of different structure are available for the treatment of painful inflammatory conditions, for example rheumatism, in particular nonsteroidal antiinflammatory drugs (NSAIDs). Numbered among this group of therapeutic agents is the sparingly water-soluble drug, diclofenac, the likewise sparingly water-soluble sodium salt of which is available under the registered trademark VOLTAREN® (Ciba-Geigy).

Peroral dosage forms of NSAIDs such as tablets that disintegrate in the stomach pose problems, as a local overconcentration resulting from too slow a diffusion and an insufficient distribution of the active drug in the gastric juice may occur in the course of disintegration, with the risk of irritation to the gastric mucous membrane and ulcus on prolonged administration. For this reason, NSAIDs in tablet form should be taken at mealtimes, so that the distribution otherwise effected only by diffusion may occur more rapidly and uniformly by convention of the active drug.

There is a need to provide novel oral dosage forms of NSAIDs which, even when taken outside mealtimes, effect a uniform distribution of the active drug in the gastric juice irrespective of time, and are thereby able to diminish the risk of irritation to the gastric mucous membrane caused by increased concentrations. Such dosage forms should, in addition, permit a more convenient use of diclofenac as analgesic by making possible ingestion immediately upon the onset of painful conditions, without first having to wait until a meal can be taken.

An effervescent formulation containing acetylsalicyclic acid as sparingly soluble NSAID with pronounced analgetic action has long been available, for example Alka-Seltzer effervescent tablets (Bayer AG) containing calcium carbonate as stabiliser. When such effervescent tablets dissolve, a water-soluble calcium salt of neutral taste is formed. The complete distribution of this soluble salt in water effects in the gastric juice, after ingestion of the solution, a rapid onset of analgetic action with reduced risk of irritation to the gastric mucous membrane owing to a low concentration in a large volume of fluid.

Up to now, no similar effervescent formulation, and also no other rapidly disintegrating formulation such as a powder or granules, has been available for the NSAID diclofenac and for its salts because, when such a dosage form disintegrates, the active drug cannot be converted into the therapeutically suitable form of a water-soluble salt of neutral taste. Usually the bitter taste of the active drug renders such formulations unsuitable.

It is the object of the present invention to provide a novel and therapeutically more advantageous formulation for the sparingly soluble drug diclofenac, which formulation disintegrates rapidly and has improved taste. This formulation shall effect a uniform distribution of the active drug in aqueous phase upon disintegration, without its bitter taste being noticeable.

This object is achieved by means of the present invention, which relates to a solid, rapidly disintegrating dosage form in the form of effervescent tablets for producing an aqueous suspension which is suitable for peroral administration and contains micronised diclofenac provided with a swellable coating which is permeable to water, or a correspondingly coated pharmaceutically acceptable salt of diclofenac, together with pharmaceutically acceptable excipients.

The invention relates preferably to effervescent tablets containing diclofenac having an average particle size smaller than 200 μm, more particularly smaller than 100 μm, suitable for effervescent formulations, suspending agents, and further optional pharmaceutical excipients.

Addition of water to the effervescent tablet results in the formation of a suspension, accompanied by the evolution of $CO_2$ gas. This suspension is stable over the time span of ca. 5–10 minutes required to ingest it without sedimentation of solid, and has a neutral or pleasant taste. After disintegration of the dosage form, diclofenac can be suspended is water and liberated in the stomach by providing the diclofenac with a coating of high permability, for example polyvinylpyrrolidone or with a dimethylaminoethylmethacrylate/methacrylate copolymer of the EUDRAGIT E type (Röhm Pharma), and of suitable layer thickness, which coating is soluble in the gastric juice. The rapid release of the active drug is of importance whenever painful conditions are to be treated immediately upon their occurrence within a short time and a rapid onset of action is desired with higher doses, while substantially avoiding the risk of irritation to the gastric mucous membrane. The choice of a coating of low permeability, for example an acrylate/methacrylate copolymer of the EUDRAGIT NE type and, if desired, of greater thickness, makes it possible to delay the release of the active drug in the stomach with corresponding prolongation of the duration of action. The delayed release of the active drug is important when using diclofenac as antirheumatic drug in long-term therapy. Because of their easier and more convenient ingestion, aqueous suspensions with delayed release of diclofenac for oral administration constitute an advantageous alternative to conventional tablets provided with a resistant film coating. The terms and expressions used in this specification are defined as follows within the scope of the description.

The effervescent tablets of this invention disintegrate in water, accompanied by evolution of $CO_2$ gas, within three minutes, preferably within 1 minute, to form a slightly turbid aqueous potable, neutral or even pleasant tasting suspension of the active drug. The suspension shall be taken directly after the complete disintegration of the effervescent tablet.

The effervescent tablet contains diclofenac, o-(2,6-dichloroanilino)phenylacetic acid, in the form of the free acid or of a pharmaceutically acceptable salt thereof.

Particularly preferred salts of diclofenac are the sodium and potassium salts (q.v. Merck Index, Tenth Edition, No. 3066).

The micronised diclofenac salt has a preferred average particle size smaller than 200 μm, preferably smaller than 100 μm. Particles of this size are obtained by conventional communution methods, e.g. grinding in an air jet mill, ball mill or vibrator mill. Micronisation is preferably effected by per se known methods using an ultrasonics disintegrator, e.g. of the Branson Sonifier type as described e.g. in J. Pharm. Sci. 53 (9), 1040–1045 (1965), or by stirring a suspension with a high-speed agitator, for example with a stirrer of the Homorex type (supplied by Brogli & Co., Basel).

The finely particulate diclofenac, or a pharmaceutically acceptable salt thereof, is provided with a permeable, swellable coating which consists of an elastic film-like material that is permeable to water or to aqueous body fluid such as gastric or intestinal juice, and which is swellable and/or soluble in this fluid.

Elastic film-like materials which are permeable to water are, typically, hydrophilic mixtures of polyvinylpyrrolidone or of a copolymer of polyvinylpyrrolidone and polyvinyl acetate with hydroxymethyl cellulose, mixtures of poyvinylpyrrolidone with polysorbates, for example polysorbate 80, mixtures of shellac with hydroxypropyl methyl cellulose, polyvinyl acetate or the copolymer thereof with polyvinylpyrrolidone, or mixtures of water-soluble cellulose derivatives such as hydroxypropyl methyl cellulose, and water-insoluble ethyl cellulose. These actual coating agents can, if desired, be used in admixture with other auxiliaries such as talcum or wetting agents such as sorbates (for example to facilitate application).

Elastic film-like materials are, in particular, hydrophilic polyvinylpyrrolidone (PVP-povidone) having an average molecular weight of 10000–700000, hydrophilic partially etherified cellulose derivatives and hydrophilic polyacrylates, for example acrylic acid polymers or acrylic acid/methacrylate copolymers.

Examples of hydrophilic, partially etherified cellulose derivatives are lower alkyl ethers of cellulose having an average molar degree of substitution (MS) greater than 1 and smaller than 3 and an average degree of polymerisation of ca. 100–5000.

The degree substitution is a measure of the substitution of the hydroxy groups per glucose unit by lower alkoxy groups. The average molar degree of substitution (MS) is an average value and indicates the number of lower alkoxy groups per glucose unit in the polymer.

The average degree of polymerisation (DP) is also an average value and indicates the average number of glucose units in the cellulose polymer.

Lower alkyl ethers of cellulose are, for example, cellulose derivatives which are substituted at the hydroxymethyl group (primary hydroxy group) of the glucose unit forming the cellulose chains, and, in some cases, at the second and third secondary hydroxy group by $C_1$–$C_4$alkyl groups, preferably methyl or ethyl, or by substituted $C_1$–$C_4$alkyl groups, for example 2-hydroxyethyl, 3-hydroxy-n-propyl, carboxymethyl or 2-carboxyethyl.

Suitable lower alkyl ethers of cellulose are preferably cellulose derivatives which are substituted at the hydroxymethyl group (primary hydroxy group) of the glucose unit by the cited $C_1$–$C_4$alkyl or substituted $C_1$–$C_4$alkyl groups, and at the second and, in some cases, third secondary hydroxy group by methyl or ethyl groups.

Suitable lower alkyl ethers of cellulose are preferably methyl cellulose, ethyl cellulose, methyl hydroxyethyl cellulose, methyl hydroxypropyl cellulose, ethyl hydroxyethyl cellulose, hydroxy ethyl cellulose, hydroxypropyl cellulose, carboxymethyl cellulose (in salt form, for example as sodium salt) or methyl carboxymethyl cellulose (also in salt form, for example as sodium salt).

Preferred lower alkyl ethers of cellulose are methyl cellulose (DP: ca. 200–1000, MS: ca. 1.4–2.0), ethyl cellulose (DP: ca. 150–1000, MS: ca. 1.2–1.8), e.g. of the Aquacoat ® type (FMC Corp.), hydroxyethyl cellulose (DP: ca. 120–1200, MS: ca. 1.2–2.5), hydroxypropyl cellulose (DP: ca. 200–3000, MS: ca. 1.0–3.0) and methyl hydroxypropyl cellulose (DU: ca. 200–1000, MS: ca. 1.4–2.0), e.g. of the Pharmacoat ® type (Shin Etsu Corp.).

Hydrophilic polyacrylates have an average molecular weight of ca. $1.0 \times 10^5$ to $1.0 \times 10^6$ and consist of acrylic acid polymers or acrylic acid/methacrylic acid copolymers. The acid groups of the acrylic acid and/or methacrylic acid monomers are partially or completely esterified by $C_1$–$C_4$alkyl groups, especially methyl and/or ethyl groups, which ester groups may be replaced by hydrophilic groups, preferably trimethylammonium ethyl.

Preferred polyacrylates are obtainable under the registered trademark EUDRAGIT from Röhm Pharma, Weiterstadt, Federal Republic of Germany. Especially preferred are EUDRAGIT commercial forms for rapidly disintegrating film coatings, for example swellable permeable types based on acrylate/methacrylate copolymers, especially an ethyl acrylate/methyl methacrylate copolymer, preferably having an average molecular weight of 800 000, for example EUDRAGIT NE 30 D, or types that are soluble in gastric fluid such as EUDRAGIT E. When using types that resist solution in gastric fluid, such as EUDRAGIT L or S a delayed release can be achieved.

Pharmaceutically acceptable excipients are, in particular viscosity index improvers which are suitable for stablising aqueous suspensions and which inhibit sedimentation of the coated active drug diclofenac, for example natural macromolecules known as karaya gum, for example of the carrageen or Viscarin ® (Marine Colloid) type, guar gum, for example galactomannans of the Meyprogat ® type (Meyhall Chemical), especially "Meyprogats" of standard types 30, 60, 90, 120 and 150, gum arabic, sodium alginate or tragacanth, semisynthetic macromolecules, for example microcrystalline cellulose of the Avicel ® type (FMC Corp.), the cellulose ethers mentioned above, such as methyl cellulose, ethyl cellulose or propyl cellulose, with or without functional groups such as hydroxy or carboxy groups, or propylene glycol alginate, synthetic macromolecules selected from the groups consisting of polyoxyethylene, for example of the Polyox ® (Union Carbide), Carbowax ® (Goodrich) or Polyglycol ® (Dow Chemicals) type, carboxypolymethylene, for example of the Carbopol ® (Goodrich) type, polyvinyl alcohol (PVA), for example of the Polyviol ® (Wacker) or Mowiol ® (Hoechst) type, or polyvinylpyrrolidone (PVP), for example of the Kollidion ® (BASF) or Plasdone ® (GAF) type, or colloidal silicates, for example colloidal silica of the Aerosil ® (Degussa) or Cab-o-Sil ® (Cabot) type.

In addition to the excipients conventionally used for the preparation of tablets, effervescent tablets contain an agent which acts as a source of carbon dioxide as well as an agent that induces the release of carbon dioxide. Agents that act as sources of carbon dioxide are pharmaceutically acceptable mono- and dibasic salts of carbonic acid, for example alkali metal carbonates or alkali metal bicarbonates, for example sodium or potassium carbonate or sodium bicarbonate, as well as alkaline earth metal carbonates, for example calcium or magnesium carbonate, or sodium glycine carbonate. Sodium bicarbonate is the preferred source of carbon dioxide.

Agents that induce the release of carbon dioxide are preferably pharmaceutically acceptable organic acids and their acid anhydrides or acid salts which are in solid form and can be formulated to granules or tablets, without premature evolution of carbon dioxide, with the coated active drug and the other cited excipients.

Pharmaceutically acceptable acids are, for example, organic acids such as tartaric acid, malic acid, fumaric acid, adipic acid, succinic acid, ascorbic acid or maleic acid. The preferred acid is citric acid.

Pharmaceutically acceptable acid anhydrides are the corresponding anhydrides of the cited organic acids, for example citric anhydride or succinic anhydride.

Examples of pharmaceutically acceptable acid salts are solid salts of polybasic acids in which at least one additional acid function is present, for example sodium hydrogen phosphate or disodium hydrogen phosphate.

Further surface-active substances or wetting agents (surfactants) may also be used for preparing the effervescent tablets, for example anionic surfactants of the alkyl sulfate type, for example sodium, potassium or magnesium n-dodecyl sulfate, or non-ionic surfactants of the fatty acid/polyhydroxy alcoholate type, such as sorbitan monostearate or sorbitan palmitate or sobitan tristearate.

Examples of further excipients are fillers in powder form such as lactose, saccharose, sorbitol, mannitol, starch, for example potato starch, rice starch, corn starch, wheat starch or amylopectin, or cellulose, preferably microcrystalline cellulose.

Further ingredients can improve the appearance and taste of the aqueous suspension obtainable by the disintegration of the effervescent tablets. Examples of such ingredients are colourants, sugar or sweeteners.

The use of colourants can serve the purpose of enhancing the appearance as well as distinguishing the composition. Colourants approved for use in pharmacy are, for example, carotinoids, iron oxides or chlorophylls.

Examples of sugar and sweeteners are saccharose, xylitol, D-xylose, D-glucose, sorbitol, mannitol or lactose, as well as saccharin sodium, dulcin, ammonium rhizinate or sodium cyclamate.

The effervescent tablets are prepared by micronising solid particles of diclofenac, providing the microparticles with a permeable, swellable coating, and tabletting the coated composition, to which optional pharmaceutical excipients may be added.

The coating of micronised diclofenac with the above coating agents can be effected by means of conventional techniques for coating finely particulate material, for example by suspending or dissolving the coating agent, in the desired ratio, in water or in organic solvent or mixture thereof, for example in ethanol, isopropanol, acetone or methylene chloride, and adding optional additives. This preferably 4 to 6% solution or dispersion is sprayed on to the diclofenac powder or mixture thereof with other excipients, for example by means of known methods such as spray coating in a fluid bed by the air-suspension technique of Wurster, for example using Aeromatic, Glatt or Hüttlin (Kugelcoater) systems.

Flowable granules which can be mixed with the agent capable of liberating carbon dioxide such as sodium bicarbonate and the corresponding agent which induces the liberation of carbon dioxide, for example citric acid, are obtained by slow and complete removal of the solvent and sieving the residue to a preferred average particle size of ca. 50 to 200 $\mu$m.

The granules of coated active drug can be mixed in the manner described above with the above mentioned aids and fillers required for the preparation of effervescent tablets, for example lactose and cellulose as well as glidants such as polyethylene glycol, and the mixture compressed to effervescent tablets. On account of the high content of excipients, tabletting machines are used which are suitable for the manufacture of large tablets of ca. 3.5 cm diameter and up to ca. 1 cm thick. Tabletting may be carried out under moisture-free conditions or in an inert gas atmosphere. The tablets can be individually packed in foils.

The invention preferably relates to effervescent tablets containing diclofenac having an average particle size smaller than 200 $\mu$m and provided with a permeable, swellable coating, preferably less than 100 $\mu$m thick, excipients suitable for effervescent formulations, suspending aids, and further optional pharmaceutical excipients.

The invention is illustrated by the following non-limitative Examples.

EXAMPLE 1

| Effervescent tablets of diclofenac (50 mg) | |
|---|---|
| diclofenac | 50 mg |
| galactomannan (Meyprogat ® 150) | 32 mg |
| colloidal silica (Aerosil ® 200) | 1 mg |
| Eudragit ® NE 30 D, solid | 7 mg |
| polyethylene glycol 8000 | 50 mg |
| sodium bicarbonate | 825 mg |
| citric acid, anhydrous | 1160 mg |
| galactomannan (Meyprogat ® 150) | 75 mg |
| microcrystalline cellulose (Avicel ® PH 102) | 200 mg |
| | 2400 mg |

A mixture of diclofenac, the first portion of Meyprogat ® 150 and Aerosil ® 200 is sprayed in a fluid bed with an aqueous dispersion of Eudragit ® NE 30 and then dried. The coated active drug is mixed with the outer phase consisting of polyethylene glycol 8000, sodium bicarbonate, citric acid, the second portion of Meyprogat ® 150 and microcrystalline cellulose, and the homogeneous mixture is compressed in a commercial tabletting machine to effervescent tablets (diameter: 19 mm, thickness: 6 mm).

EXAMPLE 2

| Effervescent tablets of diclofenac (50 mg) | |
|---|---|
| diclofenac | 50 mg |
| galactomannan (Meyprogat ® 150) | 33 mg |
| Eudragit ® NE 30 D, solid | 7 mg |
| ground lactose | 400 mg |
| polyvinylpyrrolidone (PVP ® K 30) | 10 mg |

-continued

| Effervescent tablets of diclofenac (50 mg) | |
|---|---|
| polyethylene glycol 8000 | 50 mg |
| sodium bicarbonate | 700 mg |
| citric acid, anhydrous | 975 mg |
| galactomannan (Meyprogat ® 150) | 75 mg |
| microcrystalline cellulose (Avicel ® PH 102) | 100 mg |
| | 2400 mg |

A mixture of diclofenac and the first portion of Meyprogat ® 150 is sprayed with an aqueous dispersion of Eudragit ® NE 30 D in a fluid bed and then dried. The coated active drug is mixed with the ground lactose and PVP ® K 30 and the mixture is granulated with water. The dried kneader granulate is mixed with the outer phase consisting of polyethylene glycol 8000, sodium bicarbonate, citric acid, the second portion of Meyprogat ® 150 and microcrystalline cellulose, and the mixture is compressed to effervescent tablets.

EXAMPLE 3

| Effervescent tablets of diclofenac (50 mg) | |
|---|---|
| diclofenac | 50 mg |
| galactomannan (Meyprogat ® 150) | 33 mg |
| Eudragit ® NE 30 D, solid | 7 mg |
| ground lactose | 400 mg |
| polyvinylpyrrolidone (PVP ® K 30) | 10 mg |
| polyethylene glycol 8000 | 50 mg |
| sodium bicarbonate | 700 mg |
| citric acid, anhydrous | 950 mg |
| microcrystalline cellulose (Avicel ® PH 102) | 200 mg |
| | 2400 mg |

A mixture of diclofenac and Meyprogat ® 150 is sprayed with an aqueous dispersion of Eudragit ® NE 30 D in a fluid bed and then dried. The coated active drug is mixed with the ground lactose and PVP ® K 30 and the mixture is granulated with water. The dried kneader granulate is mixed with the outer phase consisting of polyethylene glycol 8000, sodium bicarbonate, citric acid, and microcrystalline cellulose, and the mixture is compressed to effervescent tablets.

EXAMPLE 4

| Effervescent tablets of diclofenac (50 mg) | |
|---|---|
| diclofenac | 50 mg |
| galactomannan (Meyprogat ® 150) | 32 mg |
| colloidal silica (Aerosil ® 200) | 1 mg |
| Eudragit ® NE 30 D, solid | 7 mg |
| polyethylene glycol 8000 | 50 mg |
| sodium bicarbonate | 855 mg |
| citric acid, anhydrous | 1205 mg |
| microcrystalline cellulose (Avicel ® PH 102) | 200 mg |
| | 2400 mg |

A mixture of diclofenac, Meyprogat ® 150 and Aerosil ® 200 is sprayed in a fluid bed with an aqueous dispersion of Eudragit ® NE 30 and then dried. The coated active drug is mixed with the outer phase consisting of polyethylene glycol 8000, sodium bicarbonate, citric acid, and microcrystalline cellulose, and the homogeneous mixture is compressed in a tabletting machine to effervescent tablets.

EXAMPLE 5

| Effervescent tablets of diclofenac (50 mg) | |
|---|---|
| diclofenac | 50 mg |
| galactomannan (Meyprogat ® 150) | 32 mg |
| colloidal silica (Aerosil ® 200) | 1 mg |
| Eudragit ® NE 30 D, solid | 25 mg |
| polyethylene glycol 8000 | 50 mg |
| sodium bicarbonate | 825 mg |
| citric acid, anhydrous | 1142 mg |
| galactomannan (Meyprogat ® 150) | 75 mg |
| microcrystalline cellulose (Avicel ® PH 102) | 200 mg |
| | 2400 mg |

The preparation of the effervescent tablet is as described in Example 1.

EXAMPLE 6

| Effervescent tablets of diclofenac (50 mg) | |
|---|---|
| diclofenac | 50 mg |
| galactomannan (Meyprogat ® 150) | 33 mg |
| colloidal silica (Aerosil ® 200) | 1 mg |
| Aquacoat ® ECD, solid | 20 mg |
| polyethylene glycol 8000 | 50 mg |
| sodium bicarbonate | 850 mg |
| citric acid, anhydrous | 1196 mg |
| microcrystalline cellulose (Avicel ® PH 102) | 200 mg |
| | 2400 mg |

A mixture of diclofenac, Meyprogat ® 150 and Aerosil ® 200 is sprayed in a fluid bed with an aqueous dispersion of Aquacoat ® ECD 30 and then dried. The coated active drug is mixed with the outer phase consisting of polyethylene glycol 8000, sodium bicarbonate, citric acid, and microcrystalline cellulose, and the homogeneous mixture is compressed in a tabletting machine to effervescent tablets.

EXAMPLE 7

| Effervescent tablets of diclofenac (50 mg) | |
|---|---|
| diclofenac | 50 mg |
| galactomannan (Meyprogat ® 150) | 36.7 mg |
| colloidal silica (Aerosil ® 200) | 1.1 mg |
| Cellulose HPM-603 (Pharmacoat ®) | 5.5 mg |
| polyethylene glycol 8000 | 50 mg |
| sodium bicarbonate | 850 mg |
| citric acid, anhydrous | 1206.7 mg |
| microcrystalline cellulose (Avicel ® PH 102) | 200 mg |
| | 2400 mg |

A mixture of diclofenac, Meyprogat ® 150 and Aerosil ® 200 is sprayed in a fluid bed with an aqueous solution of Pharmacoat ® and then dried. The coated active drug is mixed with the outer phase consisting of polyethylene glycol 8000, sodium bicarbonate, citric acid, and microcrystalline cellulose, and the homogeneous mixture is compressed in a tabletting machine to effervescent tablets.

EXAMPLE 8

| Effervescent tablets of diclofenac (50 mg) | |
|---|---|
| diclofenac | 50 mg |
| galactomannan (Meyprogat ® 150) | 35 mg |
| colloidal silica (Aerosil ® 200) | 1 mg |
| Eudragit ® NE 30 D | 50 mg |
| polyethylene glycol 8000 | 50 mg |

-continued

| Effervescent tablets of diclofenac (50 mg) | |
|---|---|
| sodium bicarbonate | 830 mg |
| citric acid, anhydrous | 1184 mg |
| microcrystalline cellulose (Avicel ® PH 102) | 200 mg |
| | 2400 mg |

The preparation is as described in Example 4.

| Measurement of disintegration rate | |
|---|---|
| Method | US paddle, 50 rpm |
| medium | t 60 min. 0.1N HCl, pH 1.0 |
| | t 60 min. phosphate buffer, pH 6.8 |
| Results: | % age of diclofenac after |
| 60 min. | 4 |
| 120 min. | 50 |
| 240 min. | 77 |
| 420 min. | 93 |

EXAMPLE 9

| Effervescent tablets of diclofenac (50 mg) | |
|---|---|
| diclofenac | 46.5 mg |
| galactomannan (Meyprogat ® 150) | 37 mg |
| colloidal silica (Aerosil ® 200) | 1 mg |
| polyvinylpyrrolidone K 30 | 10 mg |
| polysorbat 80 | 0.8 mg |
| polyethylene glycol 8000 powder | 60 mg |
| sodium bicarbonate | 700 mg |
| citric acid, anhydrous | 1344.7 mg |
| malbitol | 200 mg |
| | 2400 mg |

A mixture of diclofenac, Meyprogat ® 150 and Aerosil ® 200 is sprayed in a fluid bed with an aqueous dispersion of polyvinylpyrrolidone K 30 and polysorbat 80 and then dried. The coated active drug is mixed with the outer phase consisting of polyethylene glycol 8000, sodium bicarbonate, citric acid, and malbitol, and the homogeneous mixture is compressed in a tabletting machine to effervescent tablets.

What is claimed is:

1. A solid, rapidly disintegrating dosage form of an effervescent tablet for producing an aqueous suspension for peroral administration, said dosage form comprises fine particles of micronized diclofenac having an average particle size smaller than 200 m$\mu$, said particles individually coated with a coating material selected from the group consisting of polyvinylpyrrolidone, a lower alkyl ether of cellulose, and a permeable, swellable acrylate/methacrylate copolymer, or a correspondingly coated pharmaceutically acceptable salt of diclofenac, together with excipients suitable for solid effervescent formulations, suspending aids, and further optional pharmaceutical excipients.

2. An effervescent tablet according to claim 1, which contains micronised diclofenac having an average particle size smaller than 100 $\mu$m.

3. An effervescent tablet according to claim 1 which contains micronised diclofenac provided with a coating of permeable ethyl cellulose or methyl hydroxypropyl cellulose, or of a permeable, swellable ethyl acrylate/methylmethacrylate copolymer, excipients suitable for solid effervescent formulations, suspending agents and further optional excipients.

4. An effervescent tablet according to claim 3, which contains finely particulate diclofenac having an average particle size smaller than 200 $\mu$m and provided with a coating of a permeable, swellable acrylate/methyl methacrylate copolymer having an average molecular weight of ca. 800,000, a pharmaceutically acceptable carbonate salt and an organic acid, a cold-water-soluble hydrocolloid as suspending agent, and further optional excipients.

* * * * *

UNITED STATES PATENT AND TRADEMARK OFFICE
CERTIFICATE OF CORRECTION

PATENT NO. : 5,211,957
DATED     : May 18, 1993
INVENTOR(S) : HAGEMANN ET AL

It is certified that error appears in the above-identified patent and that said Letters Patent is hereby corrected as shown below:

Column 10,

In claim 1, line 5, after "200" delete "m$\mu$" and insert

--$\mu$m--.

Signed and Sealed this

Eleventh Day of January, 1994

Attest:

BRUCE LEHMAN

*Attesting Officer*       Commissioner of Patents and Trademarks